(12) United States Patent
Park et al.

(10) Patent No.: US 8,426,599 B2
(45) Date of Patent: Apr. 23, 2013

(54) METHOD FOR PREPARATION OF MONTELUKAST ACID IN IONIC LIQUID MEDIUM

(75) Inventors: Chul-Hyun Park, Seongnam-si (KR); Eun-Ju Park, Seoul (KR); Choong-Hahn Kim, Seoul, KS (US); Suk Man Jang, Yongin-si (KR); Eun Jung Lim, Osan-si (KR); Young Kil Chang, Seoul (KR); Gwan Sun Lee, Seoul (KR); Jaeheon Lee, Yongin-si (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 155 days.

(21) Appl. No.: 12/674,118

(22) PCT Filed: Oct. 1, 2008

(86) PCT No.: PCT/KR2008/005794
§ 371 (c)(1),
(2), (4) Date: Feb. 18, 2010

(87) PCT Pub. No.: WO2009/048236
PCT Pub. Date: Apr. 16, 2009

(65) Prior Publication Data
US 2011/0105757 A1 May 5, 2011

(30) Foreign Application Priority Data
Oct. 9, 2007 (KR) .................. 10-2007-0101486

(51) Int. Cl.
C07D 215/14 (2006.01)
(52) U.S. Cl.
USPC ......................................................... 546/174
(58) Field of Classification Search .................. None
See application file for complete search history.

(56) References Cited

U.S. PATENT DOCUMENTS

| 5,523,477 | A | 6/1996 | King et al. |
| 5,614,632 | A | 3/1997 | Bhupathy et al. |
| 2007/0208178 | A1 | 9/2007 | Brand et al. |

FOREIGN PATENT DOCUMENTS

| EP | 0480717 A1 | 4/1992 |
| EP | 0737186 B1 | 10/1996 |
| KR | 10-0774088 B1 | 11/2007 |
| WO | 2005/105751 A1 | 11/2005 |
| WO | 2006/064269 A2 | 6/2006 |
| WO | 2007/044693 A2 | 4/2007 |
| WO | 2007/069261 A1 | 6/2007 |
| WO | 2007/072114 A1 | 6/2007 |
| WO | 2008/072872 A1 | 6/2008 |

OTHER PUBLICATIONS

Earle & K. Seddon, Ionic Liquids. Green Solvents for the Future, 72(7) Pure Appl. Chem. 1391-1398 (2000).*
European Patent Office, EP Search Report issued in corresponding EP Application No. 08838092.8, dated Mar. 16, 2011.
Jorapur et al., "Ionic Liquids: An Environmentally Friendly Media for Nucleophilic Substitution Reactions," Bull. Korean Chem. Soc., 2006, vol. 27, No. 3, pp. 345-354.
Kim et al., "Significantly Enhanced Reactivities of the Nucleophilic Substitution Reactions in Ionic Liquid," J. Org. Chem., 2003, vol. 68, pp. 4281-4285.
Japanese Patent Office, Japanese Office Action dated Oct. 16, 2012, issued in corresponding Japanese Application No. 2010-528789.
Canadian Patent Office, Canadian Office Action issued in corresponding CA Application No. 2,701,912, dated Mar. 28, 2012.
Cinzia Chiappe et al., "Nucleophilic Displacement Reactions in Ionic Liquids: Substrate and Solvent Effect in the Reaction of NaN$_3$ and KCN with Alkyl Halides and Tosylates," J. Org. Chem., 2003, vol. 68, pp. 6710-6715.

* cited by examiner

Primary Examiner — Janet Andres
Assistant Examiner — Timothy R Rozof
(74) Attorney, Agent, or Firm — Sughrue Mion, PLLC

(57) ABSTRACT

The present invention relates to a method for preparing Montelukast acid or its sodium salt by reacting a thiol compound with a Montelukast intermediate in the presence of a base in a medium comprising an ionic liquid compound. In accordance with the inventive method, highly pure Montelukast acid or its sodium salt, which is advantageously used as a raw material in the preparation of Montelukast, a leukotriene antagonist, can be easily prepared in a high yield.

6 Claims, No Drawings

METHOD FOR PREPARATION OF MONTELUKAST ACID IN IONIC LIQUID MEDIUM

CROSS REFERENCE TO RELATED APPLICATION

This application is a National Stage of International Application No. PCT/KR2008/005794 filed Oct. 1, 2008, claiming priority based on Korean Patent Application No. 10-2007-0101486, filed Oct. 9, 2007, the contents of all of which are incorporated herein by reference in their entirety.

FIELD OF THE INVENTION

The present invention relates to a method for preparing Montelukast acid and the sodium salt thereof.

BACKGROUND OF THE INVENTION

Montelukast acid of formula 1 or a pharmaceutically acceptable salt thereof has been known to block or inhibit the synthesis and activity of leukotrienes, and the sodium salt thereof is currently marketed by Merck as Singulair (the registered trademark).

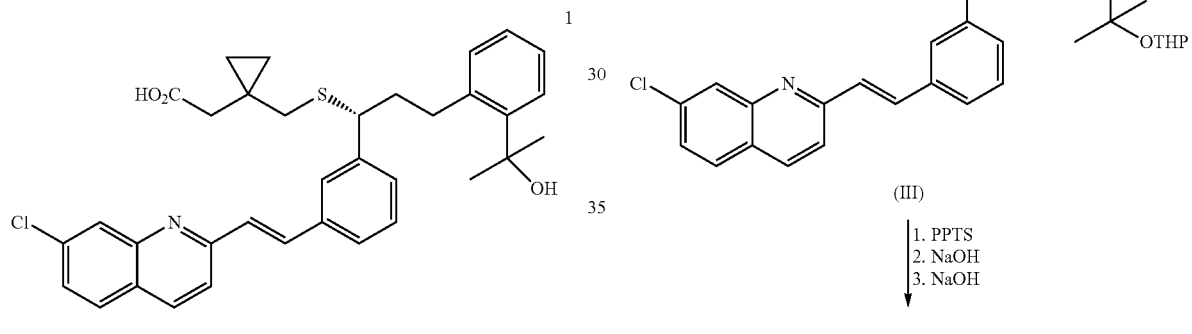

Leukotrienes are a group of local hormones derived from arachidonic acid in the body, and representative examples of leukotrienes include leukotriene B4 (LTB4), leukotriene C4 (LTC4), leukotriene D4 (LTD4) and leukotriene E4 (LTE4). The synthesis of such leukotrienes have been reported to involve the arachidonic acid metabolism by 5-lipoxygenase leading to the production of one of the known epoxides, i.e., leukotriene A4 (LTA4), which is immediately converted into other leukotrienes through successive enzymatic steps. The metabolism and biosynthesis of leukotrienes as well as their roles in certain diseases are reported in detail in [Leukotrienes and Lipoxygenases, ed. J. Rokach, Elsevier, Amsterdam (1989)].

European Patent No. 480,717 discloses a method for preparing the compound of formula 1 using a corresponding methyl ester compound, as shown in Reaction Scheme 1, which comprises the steps of: coupling methyl 1-(mercaptomethyl)cyclopropanylacetate of formula (II) with the methanesulfonyl intermediate of formula (I) in which the hydroxy group is protected by tetrahydropyranyl (THP) to obtain the methyl ester compound of formula (III); and hydrolyzing the methyl ester compound to obtain the corresponding free acid, which is directly converted into the corresponding sodium salt of formula (IV). However, the above method requires several complicated procedures such as protection; deprotection steps and column chromatographic separation of the product, which leads a low overall yield of the final product.

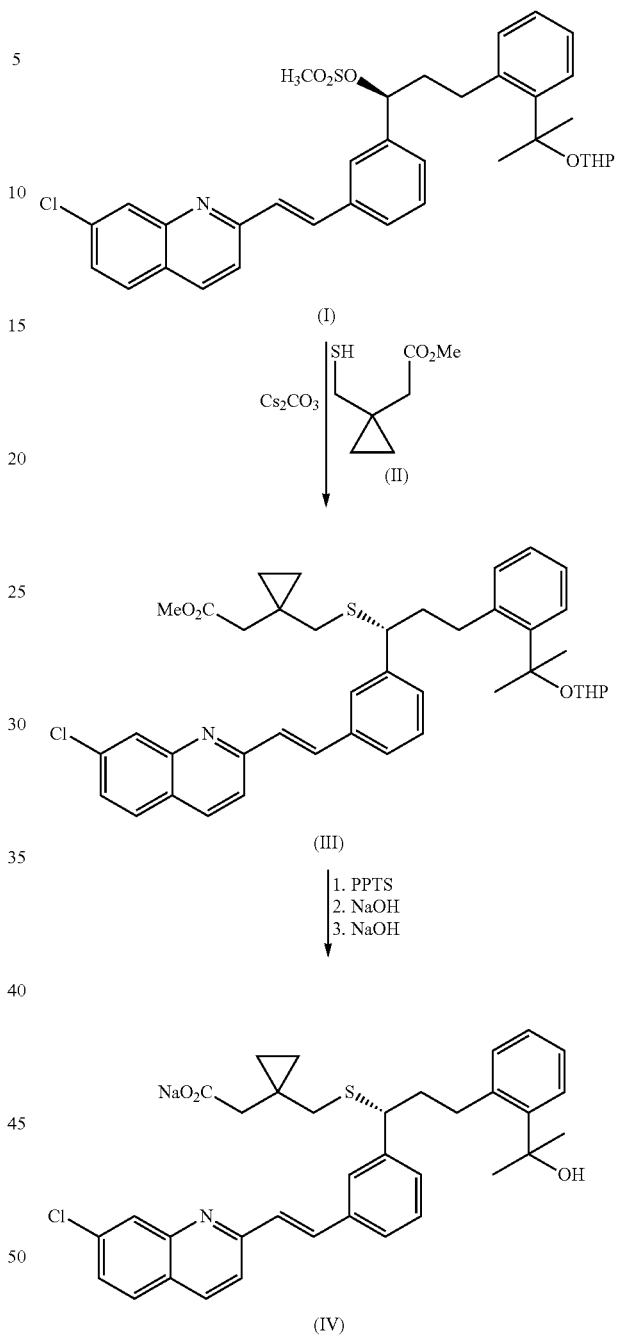

Further, in order to solve the above problem, European Patent No. 737,186 teaches a method of using the methanesulfonyl compound of formula (V) having the hydroxy group unprotected and the dilithium salt of 1-(mercaptomethyl)cyclopropanyl acetic acid of formula (VI), as shown in Reaction Scheme 2, so as to avoid the cumbersome protection; deprotection steps used in Reaction Scheme 1. This method further comprises the steps of adding dicyclohexylamine to the Montelukast acid obtained in the coupling reaction to obtain the dicyclohexylamine salt of Montelukast acid of formula (VII) in a good yield; and treating that salt with NaOH to obtain Montelukast sodium salt of formula (IV).

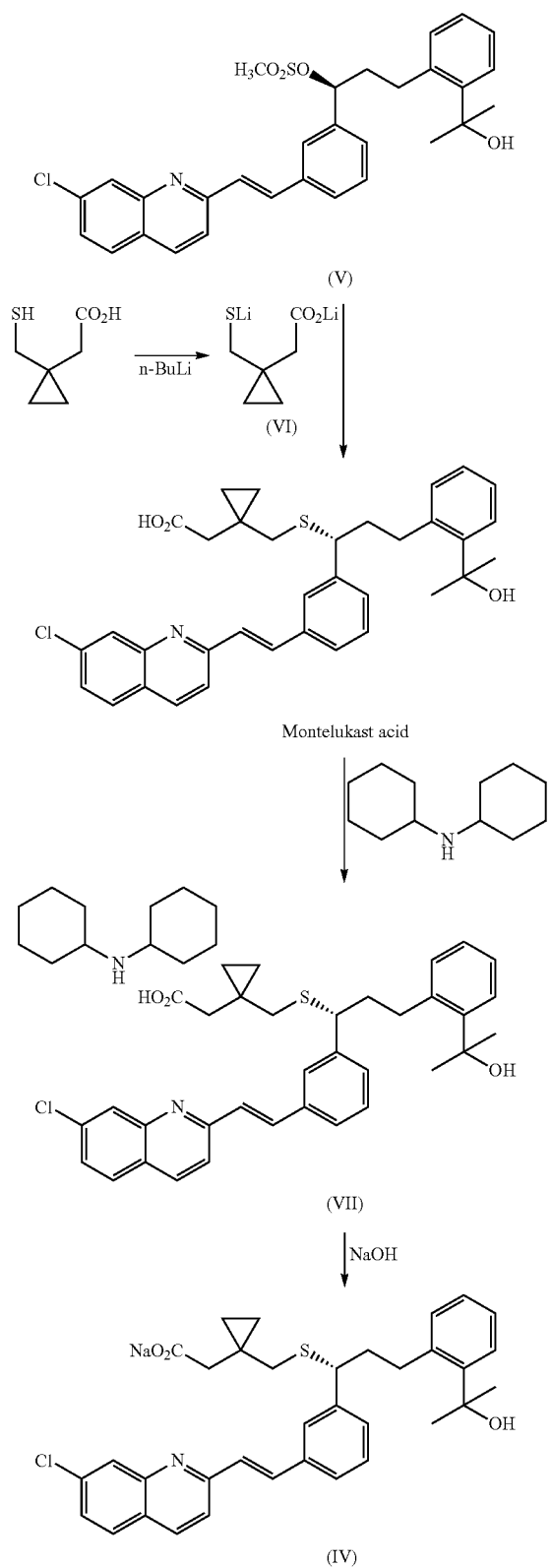

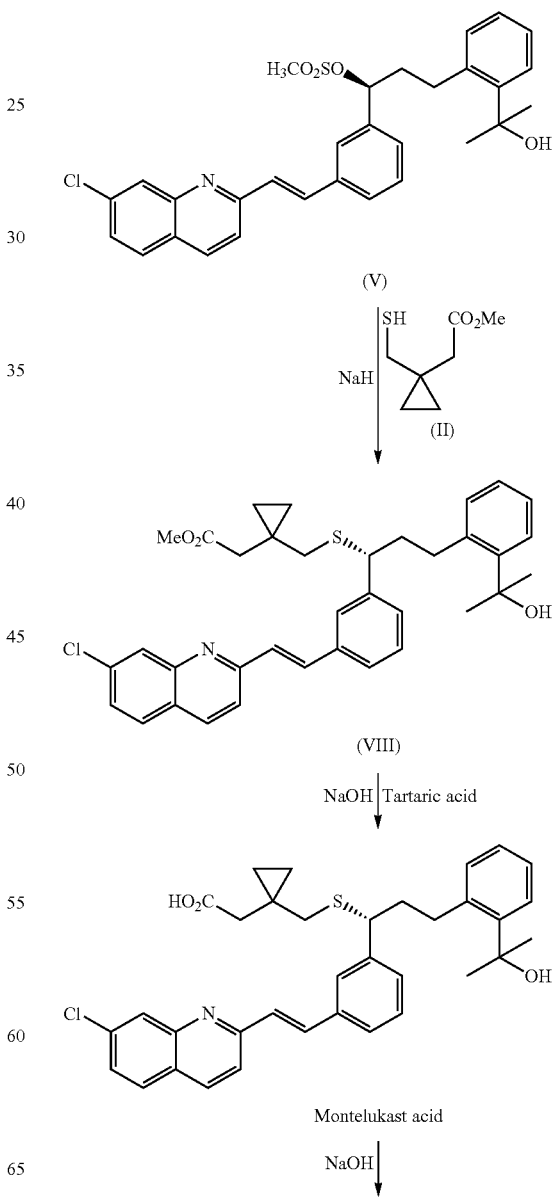

lithium. Further, the reaction must be conducted immediately at a very low temperature of −30° C. because of the sensitivity of the compound of formula (VI) to moisture and air.

Meanwhile, International Patent Publication No. WO 2005/105751 discloses a method for preparing Montelukast sodium salt of formula (IV), as shown in Reaction Scheme 3, which comprises the steps of: coupling the methanesulfonyl compound of formula (V) and methyl 1-(mercaptomethyl)-cyclopropylacetate of formula (II) in the presence of a base, e.g., LiOH, NaOH, NaH, NaOCH₃, BuLi, LiOCH₃, LiNPr₂, and potassium t-butoxide (KOt-Bu) to obtain the methyl ester of formula (VIII); hydrolyzing and acidifying the compound of formula (VIII) to obtain Montelukast acid; and treating the resulting compound with NaOH, NaOCH₃, or sodium t-butoxide (NaOt-Bu) to obtain Montelukast sodium salt of formula (IV).

However, it is very difficult to prepare the compound of formula (VI) used in the coupling reaction of the above method due to the use of spontaneously combustible n-butyl- -continued

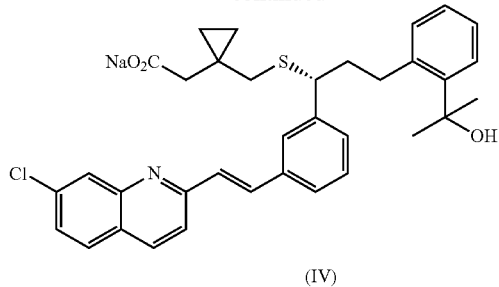

(IV)

However, the above patent teaches that the purity and yield of Montelukast acid produced by the above method are 94% and 64%, respectively, and the purity and yield of sodium montelukast, 97% and 50%, respectively, which suggests that the purity of Montelukast sodium salt obtained by this method cannot reach the required material purity of 99.3%. Accordingly, this method requires a supplementary purification procedure which is very complicated, leading to an overall yield of only 20% or less.

During the preparation of Montelukast, various structurally related impurities may form, the contents of which are required to meet specified levels, as shown in Table 1.

TABLE 1

| Impurity | Structure | Required |
|---|---|---|
| A | 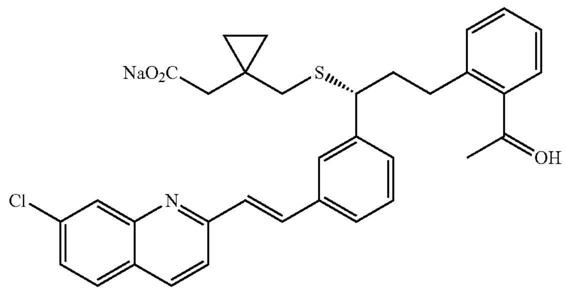 | Less than 0.1% |
| B | 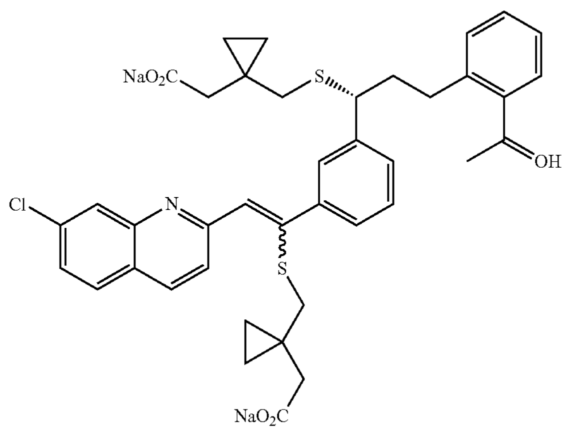 | Less than 0.2% |
| C | 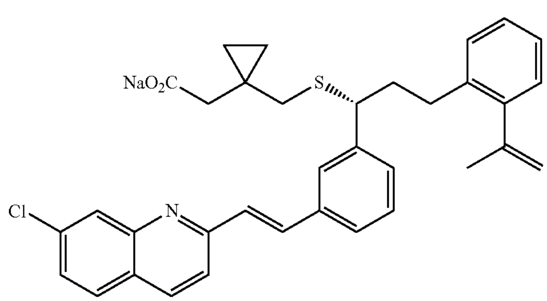 | Less than 0.35% |

TABLE 1-continued

| Impurity | Structure | Required |
|---|---|---|
| D | 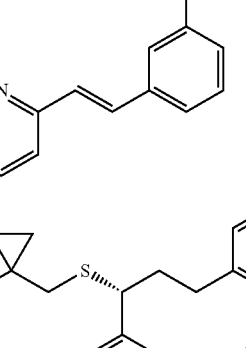 | Less than 0.1% |
| E | 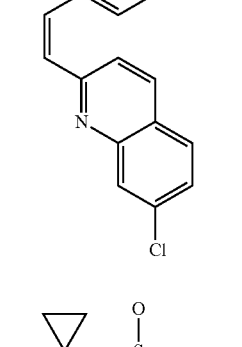 | Less than 0.1% |
| F | 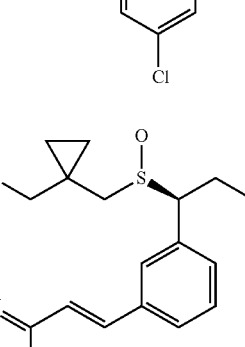 | Less than 0.2% |

Moreover, the level of the combined total impurities must not exceed 0.7% of the Montelukast sodium salt product, and accordingly, the purity of Montelukast acid, the precursory compound of Montelukast sodium salt, must be high, in the range of 98% to 99%. However, it is difficult to meet such requirement when the conventional methods are used.

SUMMARY OF THE INVENTION

Accordingly, it is an object of the present invention to provide an efficient and economical method for preparing highly pure Montelukast acid and the sodium salt thereof with a high yield.

In accordance with one aspect of the present invention, there is provided a method for preparing Montelukast acid of formula 1 or the sodium salt thereof, comprising the step of coupling a thiol compound of formula 2 with a Montelukast intermediate of formula 3 in the presence of a base in a medium comprising an ionic liquid compound selected from the group consisting of the compounds of formulae 4a to 4e:

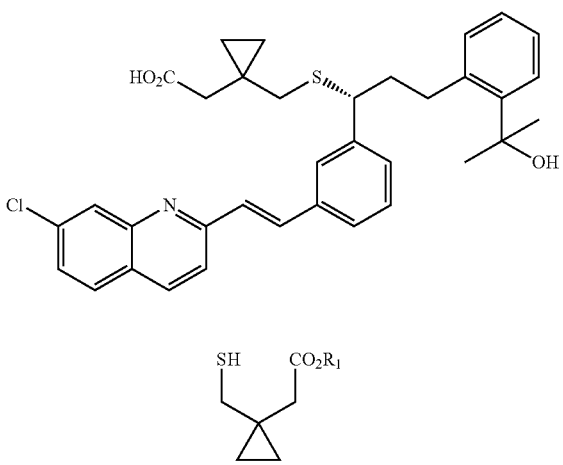

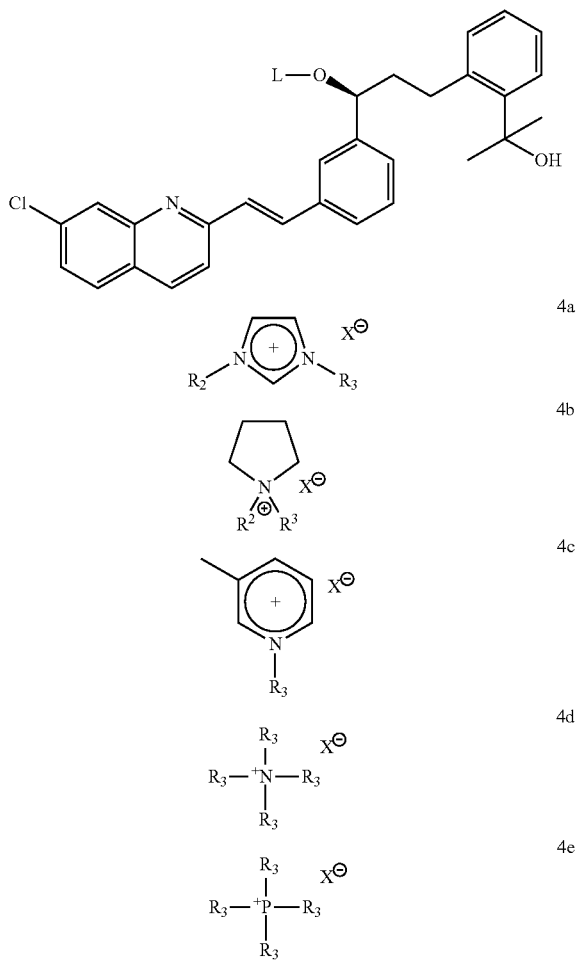

3

4a

4b

4c

4d

4e wherein, $R_1$ is hydrogen, methyl, or ethyl;
L-O is a leaving group;
$R_2$ and $R_3$ are each independently hydrogen or $C_{1-12}$ alkyl; and
X is Cl, Br, $BF_4$, $PF_6$, $SbF_6$, bis((trifluoromethane)sulfonyl)imide ($NTf_2$), (trifluoromethane)sulfonate (OTf), acetate (OAc), $NO_3$, or methanesulfonate.

DETAILED DESCRIPTION OF THE INVENTION $R_1$ of the thiol compound of formula 2 may be hydrogen, methyl or ethyl, preferably hydrogen, which makes it possible to conduct the inventive method without the use of a hydrolyzing step. In the present invention, the thiol compound may be employed in an amount of 1 equivalent or more, preferably 1 to 3 equivalents based on the compound of formula 3. The thiol compound of formula 2 is commercially available (e.g., Iffect, etc., Changzhou United Chemical) or it may be prepared by a conventional method (U.S. Pat. Nos. 5,614,632 and 5,523,477).

Representative examples of the L of the compound of formula 3 include alkylsulfonyl, arylsulfonyl, dialkylphosphoryl and diarylphosphoryl, in which alkyl may be methyl or ethyl, and aryl may be phenyl or p-tolyl. The sulfonyl group may be methanesulfonyl or p-toluenesulfonyl, and the methanesulfonyl compound may be prepared by the conventional method described in U.S. Pat. No. 5,614,632. The phosphoryl group may be dimethylphosphoryl, diethylphosphoryl or diphenylphosphoryl, preferably diphenylphosphoryl, which may be prepared by the conventional method described in Korean Patent Application No. 2006-0127942.

Representative examples of the ionic liquid compounds of formulae 4a to 4e include 1-ethyl-3-methylimidazolium bromide, 1-ethyl-3-methylimidazolium hexafluorophosphate, N-butyl-N-methylpyrrolidium bromide, N-butyl-N-methylpyrrolidium hexafluorophosphate, N-butyl-3-methylpyridium bromide, N-butyl-3-methylpyridium hexafluorophosphate, tetra-N-butylammonium bromide, tetra-N-butylammonium hexafluorophosphate, tetra-N-butylphosphonium bromide and tetra-N-butylphosphonium hexafluorophosphate, preferably N-butyl-N-methylpyrrolidium hexafluorophosphate and 1-ethyl-3-methylimidazolium bromide.

In the present invention, the ionic liquid compound may be employed in an amount ranging from 0.1 to 100 times, preferably 0.5 to 10 times the weight of the compound of formula 3, and when the amount of the ionic liquid compound is out of the above range, it is difficult to attain the expected product purity and yield.

The base used for the formation of the thiol anion during the coupling reaction may be potassium t-butoxide (KOt-Bu), sodium t-butoxide (NaOt-Bu), NaH, NaOH or KOH, preferably KOt-Bu, which may be employed in an amount of 1 or more equivalents based on the compound of formula 2, and in an amount ranging from 1.5 to 3.0 equivalents, preferably 1.8 to 2.0 equivalents based on the compound of formula 2, when $R_1$ is hydrogen. Further, when $R_1$ is methyl or ethyl, the base may be used in an amount ranging from 0.6 to 2.0 equivalents, preferably 0.9 to 1.0 equivalent based on the compound of formula 2. When the amount is less than the above range, the reaction becomes sluggish, and when more than the above range, the product purity becomes poor.

The reaction may be conducted in a solvent which may be dimethylsulfoxide, dimethylformamide, acetonitrile or tetrahydrofurane, preferably dimethylsulfoxide, at a temperature ranging from −10° C. to 50° C. The reaction may be completed within 1 hr when conducted at room temperature.

If the compound of formula 2 wherein $R_1$ is hydrogen is coupled with the intermediate of formula 3 without the ionic liquid compound, various impurities can form in excessive amounts. Also, when the reaction time is extended, the thiol compound undergoes undesirable degradations.

It must be noted that when said coupling reaction is conducted without the ionic liquid compound, the reaction becomes sluggish and does not proceed smoothly in a short time, while when the ionic liquid compound of the present invention is used, the reaction proceeds smoothly within 1 hr even when the base and the compound of formula 2 are used in required minimal amounts. Further, the product obtained in the inventive method exhibits a high purity and the inventive method gives a yield markedly higher than those realized with the conventional methods.

Montelukast sodium salt can be easily obtained by treating Montelukast acid prepared by the inventive method with NaOH, $NaOCH_3$ or sodium t-butoxide (NaOt-Bu) according to a conventional method.

The following Examples are intended to further illustrate the present invention without limiting its scope.

PREPARATION EXAMPLE 1

Preparation of 2-(2-(3(S)-(3-(2-(7-chloro-2-quinolinyl)ethenyl)phenyl)-3-methanesulfonyl-oxypropyl)phenyl)-2-propanol 100 g of 2-(2-(3(S)-(3-(2-(7-chloro-2-quinolinyl)-ethenyl)-phenyl)-3-hydroxylpropyl)phenyl)-2-propanol (Sinochem Ningbo, China) was dissolved in a mixture of 285 ml of toluene and 712 ml of acetonitrile, and 44 ml of diisopropylethylamine was added dropwise thereto. Then, after cooling the resulting mixture to −25° C., 18.4 ml of methanesulfonylchloride was slowly added dropwise thereto, and stirred at the same temperature for 2.5 hrs. After the product was observed to form, the mixture was further stirred at −25° C. for 2 hrs, and then at −35° C. for 2 hrs to complete the reaction. The resulting mixture was filtered under a nitrogen atmosphere at 0° C. to 5° C., and the filtrate was concentrated under a reduced pressure at 0 to 5° C. for 12 hrs to obtain 91 g of the title compound as a yellow solid (yield: 78.1%).

$^1$H NMR Data (300 MHz, CDCl$_3$): δ 8.1 (2H, m), 7.69 (5H, m), 7.41 (5H, m), 7.19 (3H, m), 5.70 (1H, dd), 3.25 (1H, m), 3.04 (1H, m), 2.76 (3H, s), 2.45 (1H, m), 1.92 (1H, s), 1.65 (6H, s).

PREPARATION EXAMPLE 2

Preparation of 2-(2-(3-(S)-(3-(2-(7-chloro-2-quinolinyl)-ethenyl)phenyl)-3-diphenylphosph ate oxypropyl)phenyl)-2-propanol 20 g of 2-(2-(3-(S)-(3-(2-(7-chloro-2-quinolinyl)-ethenyl)-phenyl)-3-hydroxypropyl)-phenyl)-2-propanol (Sinochem Ningbo, China) was dissolved in 240 ml of a mixture of methylene chloride and toluene (2:1), and 7.31 ml of triethylamine was added dropwise thereto. Then, 13.6 ml of diphenyl chlorophosphate was slowly added dropwise to the resulting mixture, followed by adding 1.06 g of 4-dimethylaminopyridine dropwise thereto. After confirming the completion of the reaction by TLC (thin layer chromatography) after 1 hr, the resulting mixture was combined with 100 ml of methylene chloride and 200 ml of distilled water, the organic layer was separated, dried over sodium sulfate, and concentrated under a reduced pressure. The residue was recrystallized using 60 ml of a mixture of ethyl acetate and n-hexane (1:3), filtered, washed with 40 ml of distilled water, and dried in warm air, to obtain 29.5 g of the title compound as a yellow solid (yield: 97.8%).

M.P.: 127° C.

$^1$H NMR (300 MHz, CDCl$_3$): δ 8.4 (1H, d), 7.94 (1H, d), 7.75 (3H, m), 6.97-7.35 (20H, m), 5.70-5.72 (1H, m), 3.02-3.09 (2H, m), 2.29-2.34 (2H, m), 1.65 (3H, s), 1.59 (3H, s).

Preparation of 1-(((1-(R)-(3-(2-(7-chloro-2-quinolidyl)ethenyl)phenyl)-3-(2-(1-hydroxy-1-methylethyl)phenyl)propyl)thio)methyl)cyclopropane acetic acid (Montelukast acid)

EXAMPLE 1

15 g of 1-ethyl-3-methylimidazolium bromide was dissolved in 60 ml of dimethylsulfoxide, 3.15 g of 1-(mercaptomethyl)cyclopropanylacetic acid (Changzhou United Chemical, China) was added thereto, and then, 2.42 g of potassium t-butoxide was rapidly added to the mixture at 10° C., followed by stirring the resulting mixture for 5 min. After rapidly adding 2.42 g of potassium t-butoxide, the resulting mixture was further stirred at the same temperature for 10 min. Then, 10 g of the compound obtained in Preparation Example 2 was added to the mixture at 15~17° C., followed by stirring the resulting mixture for 1 hr to complete the reaction.

After adding 30 ml of n-heptane to the mixture obtained above, 500 ml of ice water and 300 ml of tetrahydrofurane were successively added thereto, the organic layer was separated and the aqueous layer was extracted with 500 ml of ethyl acetate. The combined organic layer was washed 3 times with 200 ml of saturated liquid ammonium chloride, dried over sodium sulfate, and concentrated under a reduced pressure. The residue thus obtained was recrystallized, using 60 ml isopropanol and 30 ml of purified water, and the resulting solid was filtered and dried under a vacuum to obtain 7.9 g of the title compound (yield: 93%, purity: 98.6%).

$^1$H NMR (300 MHz, CD$_3$OD): δ 8.27 (1H, d), 7.98 (1H, s), 7.78 (2H, d), 7.73 (2H, d), 7.38-7.56 (6H, m), 7.07-7.14 (3H, m), 4.84 (1H, t), 3.30-3.33 (1H, m), 2.84-2.87 (1H, m), 2.52 (2H, s), 2.41 (2H, s), 2.18-2.23 (2H, m), 1.55 (6H, s), 0.37-0.52 (4H, m).

EXAMPLE 2

14 g of N-butyl-N-methylpyrrolidium bromide was dissolved in 60 ml of dimethylsulfoxide, 2.7 g of 1-(mercaptomethyl)cyclopropanylacetic acid (Changzhou United Chemical, China) was added thereto, and then, 4.0 g of potassium t-butoxide was rapidly added dropwise to the mixture at room temperature, followed by stirring the resulting mixture for 30 min. 5 g of the compound obtained in Preparation Example 2 was added thereto, the resulting mixture was stirred for 30 min to complete the reaction, and 50 ml of purified water and 50 ml of ethyl acetate were added thereto. The combined organic layer was separated, dried over sodium sulfate, concentrated under a reduced pressure, and recrystallized using 30 ml of isopropanol and 10 ml of purified water. The resulting solid was filtered and dried under a vacuum to 2.98 g of the title compound (yield: 70.2%, purity: 98.7%).

$^1$H NMR data were the same as described in Example 1.

EXAMPLE 3

15 g of N-butyl-N-methylpyrrolidium hexafluorophosphate was dissolved in 60 ml of dimethylsulfoxide, 3.7 g of methyl 1-(acetylthiomethyl)cyclopropanylacetate was added thereto, and 2.4 g of potassium t-butoxide was rapidly added dropwise to the mixture at room temperature, followed by stirring the resulting mixture for 30 min. Then, after adding 10 g of the compound obtained in Preparation Example 2 thereto, the resulting mixture was stirred for 30 min to complete the reaction, and 100 ml of purified water and 100 ml of ethyl acetate were added thereto. The combined organic layer was separated, dried over sodium sulfate, and concentrated under a reduced pressure. The resulting residue was dissolved in a mixture of 29 ml of tetrahydrofurane and 29 ml of methanol, 29 ml of 10% aqueous NaOH was slowly added thereto at 10° C., and the resulting mixture was stirred at room temperature for 5 hrs to complete the reaction. After adding 100 ml of water and 100 ml of ethyl acetate to the mixture obtained above, the combined organic layer was separated, dried over sodium sulfate, concentrated under a reduced pressure, and recrystallized using 60 ml of isopropanol and 20 ml of purified water. The resulting solid was filtered and dried under a vacuum to obtain 7.7 g of the title compound (yield: 90.2%, purity: 99.0%).

$^1$H NMR data were the same as described in Example 1.

EXAMPLE 4

30 g of 1-ethyl-3-methylimidazolium bromide was dissolved in 1200 ml of dimethylsulfoxide, 9.6 g of methyl 1-(acetylthiomethyl)cyclopropanylacetate was added thereto, and then, 6.3 g of potassium t-butoxide was rapidly added dropwise to the mixture at room temperature, followed by stirring the resulting mixture for 30 min. Then, 20 g of the compound obtained in Preparation Example 1 was added to the mixture, the resulting mixture was stirred for 30 min to complete the reaction, and 200 ml of purified water and 200 ml of ethyl acetate were added thereto. The combined organic layer was separated, dried over sodium sulfate, and concentrated under a reduced pressure. The residue thus obtained was dissolved in a mixture of 58 ml of tetrahydrofurane and 58 ml of methanol, 58 ml of 10% aqueous NaOH was slowly added thereto at 10° C., and the resulting solution was stirred at room temperature for 5 hrs to complete the reaction. After adding 200 ml of purified waster and 200 ml of ethyl acetate thereto, the combined organic layer was separated, dried over sodium sulfate, concentrated under a reduced pressure, and recrystallized using 120 ml of isopropanol and 40 ml of purified water. The resulting solid was filtered and dried under a vacuum to obtain 18.0 g of the title compound (yield: 82.6%, purity: 98.1%).

$^1$H NMR data were the same as described in Example 1.

COMPARATIVE EXAMPLE 1

A Conventional Method Described in International Patent Publication No. WO 2005/105751

Step 1)

2.04 g of 60% sodium hydride was added to 80 ml of tetrahydrofurane, a mixture obtained by mixing 11.7 g of methyl 1-(acetylthiomethyl)cyclopropanyl acetate with 20 ml of tetrahydrofurane was rapidly added thereto at room temperature, followed by stirring the resulting mixture for 1 hr. After adding 100 ml of dimethylformamide thereto, 80 ml of a tetrahydrofurane containing 25% the compound obtained in Preparation Example 1, which was cooled to −5° C., was added thereto, and the resulting mixture was stirred at room temperature for 4 hrs. After adding 200 ml of ethyl acetate and 400 ml of 5% aqueous NaCl thereto, the combined organic layer was separated, washed 2 times with 100 ml of purified water, dried over sodium sulfate, and concentrated under a reduced pressure to remove the solvent, to obtain 29.5 g of an oil containing 75% 1-(((1(R)-(3-(2-(7-chloro-2-quinolidyl)ethenyl)phenyl)-3-(2-(1-hydroxy-1-methyl-ethyl)phenyl)-propyl)-thio)-methyl)cyclopropanyl acetic acid methyl ester.

Step 2)

The residue obtained in Step 1 was dissolved in 58.9 ml of tetrahydrofurane and 29.5 ml of methanol, and 58.9 g of 10% NaOH was added thereto, followed by stirring the mixture overnight at room temperature. After adding 85.4 ml of toluene to the resulting mixture, the combined organic layer was separated, and the pH was adjusted to 4 using 0.5 M tartaric acid. The combined organic layer was separated, concentrated under a reduced pressure to adjust its total volume to about 60 ml, and stirred at room temperature to be recrystallized. The resulting solid was filtered and dried under a vacuum to obtain 18.2 g of the title compound (yield: 83.1%, purity: 93.3%).

COMPARATIVE EXAMPLE 2

A Method not Using an Ionic Liquid Compound 5.5 g of 1-(mercaptomethyl)cyclopropanylacetic acid (Changzhou United Chemical, China) was dissolved in 60 ml of dimethylsulfoxide, 8.2 g of potassium t-butoxide was rapidly added thereto at room temperature, followed by stirring the mixture for 30 min. Then, after adding 10 g of the compound obtained in Preparation Example 2 to the mixture, the resulting mixture was stirred for 8.5 hrs, and 100 ml of purified water and 100 ml of ethyl acetate were added thereto. The combined organic layer was dried over sodium sulfate, concentrated under a reduced pressure to remove the solvent, and recrystallized using 60 ml of isopropanol and 20 ml of purified water. The resulting solid was filtered and dried under a vacuum to obtain 1.2 g of the title compound (yield: 14.1%, purity: 92%).

COMPARATIVE EXAMPLE 3

A Method for Preparing dicyclohexylamine 1-(((1 (R)-(3-(2-(7-chloro-2-quinolidyl)ethenyl)phenyl)-3-(2-(1-hydroxy-1-methyl-ethyl)phenyl)propyl)thio) methyl)cyclopropanyl acetate Described in European Patent No. 737,186)

5.9 g of 1-(mercaptomethyl)cyclopropaneacetic acid was dissolved in 140 ml of tetrahydrofurane and cooled to −15° C., and 47 ml of a hexane containing 1.6 M n-butyllithium was slowly added dropwise thereto, followed by stirring the mixture for 30 min. Then, a solution obtained by dissolving 20 g of 2-(2-(3(S)-(3-(2-(7-chloro-2-quinolinyl)ethenyl)phenyl)-3-methane-sulfonyl-oxypropyl)phenyl)-2-propanol in 80 ml of tetrahydrofurane was added dropwise thereto at −5° C. for 30 min, and the resulting solution was stirred at the same temperature for 8.5 hrs. After adding 240 ml of ethyl acetate and 240 ml of 10% aqueous NaCl thereto, the combined organic layer was separated, washed with 10% tartaric acid, dried over sodium sulfate, and concentrated under a reduced pressure to remove the solvent. The residue thus obtained was mixed with 240 ml of ethyl acetate and 8 ml of dicyclohexylamine, followed by stirring the resulting mixture for 2 hrs. Then, after adding 240 ml of n-hexane to the resulting mixture, the obtained solution was stirred overnight to obtain 17.4 g of the title compound (yield: 60%, purity: 74%).

$^1$H NMR Data (300 MHz, CD$_3$OD): δ 8.30 (1H, d), 8.01 (1H, s), 7.85-7.92 (2H, m), 7.85-7.92 (2H, m), 7.79 (1H, s), 7.73 (1H, s), 7.53-7.54 (2H, m), 7.40-7.45 (4H, m), 7.11-7.16 (3H, m), 4.05 (1H, t), 3.12-3.13 (3H, m), 3.10-3.12 (1H, m), 2.65 (1H, d), 2.56 (1H, d), 2.38 (1H, d), 2.36 (1H, d), 2.28-2.33 (2H, m), 2.03-2.06 (4H, m), 1.87-1.88 (4H, m), 1.84 (2H, d), 1.28-1.39 (10H, m), 1.54 (6H, s), 0.39-0.52 (4H, m)

While the invention has been described with respect to the above specific embodiments, it should be recognized that various modifications and changes may be made to the invention by those skilled in the art which also fall within the scope of the invention as defined by the appended claims.

We claim:

1. A method for preparing Montelukast acid of formula 1 or the sodium salt thereof, comprising coupling a thiol compound of formula 2 with a Montelukast intermediate of formula 3 in the presence of a base in a medium comprising an ionic compound selected from the group consisting of 1-ethyl-3-methylimidazolium bromide, and N-butyl-N-methylpyrrolidium hexafluorophosphate to give the Montelukast acid of formula 1; and optionally reacting the obtained Montelukast acid with NaOH, NaOCH$_3$ or sodium butoxide to give Montelukast sodium salt;

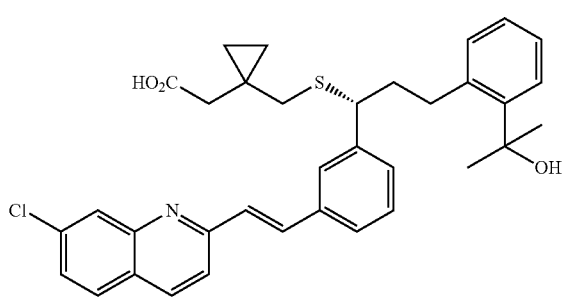

1

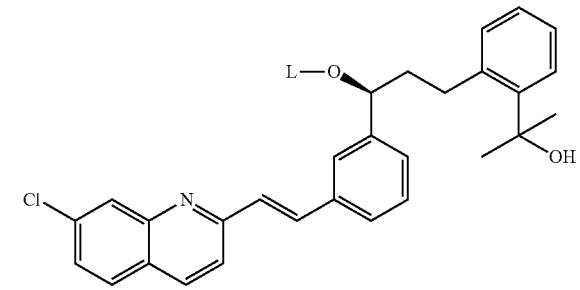

3 wherein $R_1$, is hydrogen, methyl, or ethyl; and
L-O is a leaving group.

2. The method of claim 1, wherein L is selected from the group consisting of methanesulfonyl, p-toluenesulfonyl, dimethylphosphoryl, diethylphosphoryl and diphenylsphosphoryl.

3. The method of claim 2, wherein L is diphenylsphosphoryl.

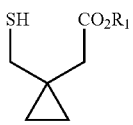

2

4. The method of claim 1, wherein the ionic liquid compound is employed in an amount ranging from 0.1 to 100 times the weight of the compound of formula 3.

5. The method of claim 1, wherein the base is selected from the group consisting of potassium t-botoxide, sodium t-botoxide, NaH, NaOH, and KOH.

6. The method of claim 5, wherein the base is potassium t-botoxide.

* * * * *